United States Patent
Bernard et al.

(10) Patent No.: US 12,144,901 B2
(45) Date of Patent: Nov. 19, 2024

(54) TREATMENT METHOD FOR RADIATION STERILIZATION OF CONTAINERS MADE FROM THERMOPLASTIC MATERIAL

(71) Applicant: SIDEL PARTICIPATIONS, Octeville-sur-Mer (FR)

(72) Inventors: Véronique Bernard, Octeville-sur-Mer (FR); Nicolas Chomel, Octeville-sur-Mer (FR); Anthony Le Pechour, Octeville-sur-Mer (FR)

(73) Assignee: SIDEL PARTICIPATIONS, Octeville-sur-Mer (FR)

( * ) Notice: Subject to any disclaimer, the term of this patent is extended or adjusted under 35 U.S.C. 154(b) by 746 days.

(21) Appl. No.: 17/292,424

(22) PCT Filed: Oct. 30, 2019

(86) PCT No.: PCT/FR2019/052577
§ 371 (c)(1),
(2) Date: May 7, 2021

(87) PCT Pub. No.: WO2020/094948
PCT Pub. Date: May 14, 2020

(65) Prior Publication Data
US 2022/0008573 A1 Jan. 13, 2022

(30) Foreign Application Priority Data
Nov. 9, 2018 (FR) ...................................... 1860356

(51) Int. Cl.
*A61L 2/08* (2006.01)
(52) U.S. Cl.
CPC ........... *A61L 2/087* (2013.01); *A61L 2202/23* (2013.01)

(58) Field of Classification Search
CPC .......... A61L 2/087; A61L 2/24; A61L 2202/23
See application file for complete search history.

(56) References Cited

FOREIGN PATENT DOCUMENTS

| CN | 103770981 A | * 5/2014 | ............. A61L 2/087 |
|---|---|---|---|
| EP | 2316495 A1 | 5/2011 | |
| EP | 3360810 A1 | 8/2018 | |
| FR | 2915127 A1 | 10/2008 | |
| JP | H11114030 A | 4/1999 | |
| JP | 2007106438 A | 4/2007 | |
| JP | 2007126168 A | 5/2007 | |
| JP | 2013121852 A | 6/2013 | |
| JP | 2015093679 A | 5/2015 | |
| JP | 2018070199 A | 5/2018 | |
| WO | 03084818 A1 | 10/2003 | |
| WO | 2006136498 A1 | 12/2006 | |
| WO | 2008049876 A1 | 5/2008 | |
| WO | 2016120544 A1 | 8/2016 | |

OTHER PUBLICATIONS

Machine translation of CN-103770981-A (Year: 2014).*
International search report dated Feb. 24, 2020.

* cited by examiner

*Primary Examiner* — Timothy C Cleveland

(57) ABSTRACT

The invention proposes a treatment method for the sterilization by irradiation of containers made of thermoplastic material. The method comprises at least an initial step of modification of the pitch consisting in selectively varying the initial pitch between two consecutive containers to increase the irradiation time of each container. The method also comprises an irradiation step consisting in irradiating each container from the outside with an electron beam emitted by at least one emitter of a sterilization device.

20 Claims, 6 Drawing Sheets

TREATMENT METHOD FOR RADIATION STERILIZATION OF CONTAINERS MADE FROM THERMOPLASTIC MATERIAL

TECHNICAL FIELD OF THE INVENTION

The invention relates to a treatment method for the sterilization by irradiation of containers made of thermoplastic material.

The invention relates more particularly to a treatment method for the sterilization by irradiation of containers made of thermoplastic material, such as bottles, of the type having a main axis and comprising a body provided with a neck and closed by a bottom.

STATE OF THE ART

Various sterilization methods for sterilizing at least the inside of a preform and/or of a container made of thermoplastic material are known from the state of the art.

A container made of thermoplastic material is manufactured from a hot preform, generally previously thermally conditioned in an oven of a container manufacturing installation before being introduced into a mold to be transformed therein by blow-molding by means of at least one pressurized fluid, with or without stretching.

Different types of containers (bottles, flasks, pots, etc.) are manufactured thus which are notably, but not exclusively, intended for use for the packaging of products in the agri-food industry.

In the field of the manufacture of containers for the agri-food industry, it is sought to reduce the risks of microbiological contaminations of containers by pathogenic agents, i.e. microorganisms, by any means.

That is why the Applicant has already proposed implementing different actions for eliminating pathogenic agents, such as germs (bacteria, moulds, etc.), which are likely to affect the product contained in such containers.

The actions aiming to destroy the microorganisms to sterilize at least the inside of the container on the one hand, and the actions aiming more generally to prevent the contamination of the containers by such microorganisms on the other hand, can in particular be distinguished.

The prior art documents FR-2,915,127, WO-03/084818 and EP-2,094,312, to which reference can be made for complete details, are cited as nonlimiting examples of such actions.

The document FR-2,915,127 describes a container manufacturing installation comprising a protection enclosure delimiting a zone inside which there is arranged a container molding machine of blower type which is fed by transfer means with preforms previously thermally conditioned in an oven.

According to the teachings of this document, the installation comprises a system for injecting filtered air into the enclosure to establish therein, in particular, a pressurization so as to limit the risks of contamination both of the preforms leaving the oven and the manufactured containers.

The document WO-03/084818 describes, for example, a decontamination treatment by irradiation of the neck of preforms by a radiation of ultraviolet (UV) type, before the introduction of the preforms into the oven.

The document EP-2,094,312 describes, for example, a treatment by irradiation with an ultraviolet (UV) radiation implemented particularly in an oven to decontaminate at least the outer surface of the preform during the thermal conditioning.

The document WO-2006/136498, in the name of the Applicant, describes, for example, a decontamination treatment of a preform consisting depositing, by condensation, a substantially uniform mist film of a sterilizing agent on the inner wall of the preform.

Such a decontamination treatment by condensation, said to be by "chemical pathway", is satisfactory since degrees of decontamination up to 6 Log are obtained.

It is recalled that the quantity of microorganisms is likely to be quantified by counting notably after washing, filtration and cultivation operations.

A logarithmic reduction of the number of microorganisms is thus determined, for example said to be of the order of 3 Log (or even 3 D) equivalent to 1000 units ($10^3$).

However, alternative solutions to decontamination by chemical pathway are sought that make it possible not to use any sterilizing agent, such as hydrogen peroxide ($H2O2$), but without, however, in any way sacrificing the result obtained for the decontamination.

In the document WO-2016/120544, the Applicant has proposed an alternative solution consisting in proceeding with the sterilization of a container made of thermoplastic material by means of a pulsed electron beam and a movable reflector.

For the industrial application of such a treatment method for the sterilization of containers, in addition to the technical control, one of the issues is, these days, essentially economic in character, given the high cost of an emitter used to obtain the electron beam.

That is why solutions are sought that make it possible to optimize the use of an emitter, reduce the total number of emitters, and do so while having the same container sterilization results.

Now, it is essential to have an irradiation time which is sufficient during the treatment to irradiate all the surfaces of the container to be sterilized with a quantity of electrons that makes it possible to obtain a lethal dose for the microorganisms.

The treatment method must also be compatible with the current container production rates, which are, for example in the case of bottles made of PET, more than 60 000 bottles per hour.

The aim of the invention is notably to propose a novel treatment method to resolve at least some of the drawbacks of the state of the art and in particular, reduce the number of emitters and optimize the use thereof for each type of container.

BRIEF SUMMARY OF THE INVENTION

To this end, the invention proposes a treatment method for the sterilization by irradiation of containers made of thermoplastic material of the type having a main axis and comprising a body provided with a neck and closed by a bottom, wherein the containers forming a flow are transported by a conveying system along a given path, with a determined separation, called pitch, corresponding to the distance between the axes of two consecutive containers, the treatment method comprising at least:
   an initial step of modification of the pitch consisting in selectively varying said initial pitch between two consecutive containers to increase the irradiation time of each container;
   a irradiation step consisting in irradiating each container of the flow from the outside with an electron beam emitted by at least one emitter of a sterilization device which is arranged on a section of said path so as to form a container irradiation zone.

Advantageously, the method according to the invention further makes it possible to reduce the number of emitters needed by virtue of the increase in the irradiation time of the containers resulting from the variation of the implementation pitch.

According to the invention, each container is irradiated with a dose which is greater than or equal to that of the prior art, that is to say a lethal dose for the microorganisms, but with a lesser number of emitters.

Advantageously, said lethal dose is thus obtained with fewer emitters because of the increase in irradiation time which results from the variation of the pitch produced selectively so as to be able to reduce the speed at least in the irradiation zone or zones, but without, however, ultimately reducing the rate, that is to say the average speed of circulation of the containers.

Advantageously, the implementation of a treatment method according to the invention is compatible with the container manufacturing rates and therefore lends itself to industrial application by incorporating a sterilization device for its implementation within a manufacturing installation for containers, such as bottles made of PET.

Advantageously, the sterilization of the container according to the method of the invention is performed by irradiating an empty container, before proceeding with the filling.

Preferably, the method according to the invention is implemented in a container manufacturing installation between the molding unit (or blower) and the next unit, such as a filling or labeling unit.

Depending on the applications, a labeling of the containers is in fact likely to be performed before or after the filling thereof.

By comparison with a method for decontaminating preforms by chemical pathway according to the abovementioned document WO-2006/136498, the invention makes it possible to greatly simplify the design of an installation for manufacturing containers from a preform, in particular the molding unit (or blower).

The sterilization of the final container (and not of the preform) makes it possible to dispense with numerous means hitherto implemented in such a container manufacturing installation, the microorganisms present being destroyed during the irradiation of the container by means of the electron beam, preferably of pulsed type.

Thus, it is no longer necessary to implement specific means (such as air injection systems, etc.) to preserve the sterility of a preform after its chemical treatment, that is to say during its thermal conditioning, its transformation by blow-molding or stretch-blow-molding into a container, and do so until the filling and the closing of the container.

Advantageously, the method according to the invention makes it possible to simultaneously sterilize both the inside and the outside of a container.

Thus, the devices for treating preforms by irradiation by means of a UV radiation can be eliminated.

The air injection systems and, more generally, air filtration systems participating in obtaining a clean manufacturing environment can also be eliminated.

Advantageously, the elimination of all of such devices and/or systems makes it possible to produce significant savings on the cost of a manufacturing installation and do so both on acquisition and in operation.

Advantageously, the method according to the invention is implemented in a container manufacturing installation downstream of the molding unit (or blower) such that the actions performed upstream of the molding unit, notably for the destruction of the microorganisms and the prevention of the risks of contamination of the containers, can be wholly or partly eliminated.

Advantageously, the design of the molding unit (or blower) is thereby particularly simplified and its cost, both to manufacture and to operate, reduced. In fact, the cleaning operations, called "CIP" (the acronym for Clean-In-Place) can be eliminated.

Consequently, it is no longer necessary, for the molding unit, to have to use costly materials, such as stainless steel, chosen for their resistance to chemical attack, notably corrosion, resulting from the cleaning products used in such "CIP" operations.

Advantageously, the sterilization treatment by irradiation according to the invention can be performed in combination with variant embodiments making it possible to optimize the irradiation by maximizing the dose received by each container.

Advantageously, it will be appreciated that the invention runs counter to the teachings of the state of the art that consist, to preserve the rate, in multiplying the number of emitters along the path to achieve an irradiation dose that is sufficient to sterilize each container.

According to other features of the invention:
the initial step of modification of said initial pitch consists in reducing the separation between the containers of said flow by reducing the speed of the transported containers to obtain, at least in said irradiation zone, a proximal pitch which is less than the initial pitch;
the initial step of modification of said initial pitch comprises at least one phase of deceleration of the containers to obtain said proximal pitch;
said method comprises a final step of modification of the pitch comprising at least one acceleration phase to once again vary the separation of the containers in order to reestablish said initial pitch between the containers of said flow;
said method comprises a step of division of the flow, implemented prior to the initial step of modification of the pitch, consisting in dividing the flow of transported containers, into at least:
a first flow of containers which are transported to a first irradiation zone comprising at least one first emitter capable of emitting an electron beam and
a second flow of containers which are transported to a second irradiation zone comprising at least one second emitter capable of emitting an electron beam;
the flow of containers is divided at a rate of one container in two to form, respectively, said first flow and said second flow such that the separation between two consecutive containers of one or other of said first flow and second flow is then equal to a distal pitch which is greater than the initial pitch;
after the division of the flow of containers, said initial step of modification of the initial pitch comprises at least one deceleration phase to reduce the speed of each of the containers forming one of said at least first flow and second flow at least in said associated first irradiation zone and second irradiation zone;
after the step of division of the flow of containers, said step of modification of the initial pitch comprises at least one acceleration phase to selectively increase the speed of each of the containers of said first flow and second flow, respectively upstream and/or downstream of said first irradiation zone and second irradiation zone;

said method comprises a final step of modification of the pitch consisting, after said at least one irradiation step, in merging together the containers of said first flow and second flow to obtain a flow of containers having said initial pitch between two consecutive containers;

said irradiation step comprises a first irradiation step consisting in irradiating, from the outside, at least the body of each container with the electron beam emitted by said at least one emitter having a main axis;

when the direction of displacement followed by the flow of containers is orthogonal to the main axis of the containers, said at least one emitter is arranged relative to said path in such a way that said main axis of the emitter is substantially coaxial with the main axis of the irradiated container;

when the direction of displacement followed by the flow of containers is orthogonal to the main axis of the containers, said at least one emitter is inclined by an inclination angle which, lying between the main axis of the emitter and the axis of the container, is determined as a function of the height of the container so that the ratio of the height of the container to the height of the emitter is close to 1;

when the direction of displacement followed by the flow of containers comprises at least a section that is inclined relative to the axis of said at least one emitter such that each container performs an oblique displacement following an upward or downward movement, said at least one emitter is arranged horizontally to have an inclination angle of 90° between its main axis and the axis of a container;

each container is driven in rotation on itself about its axis during at least said first irradiation step;

said irradiation step comprises a second irradiation step consisting in irradiating at least the neck of each container with an electron beam emitted by said at least one emitter which, having a main axis, is arranged plumb with the containers following said path.

Advantageously, said method comprises a final step of modification of the pitch consisting, after said at least one irradiation step, in once again varying the separation of the containers to reestablish said initial pitch between the containers of said flow.

Advantageously, said method comprises a preliminary determination step consisting, as a function of the maximum outside diameter of a container, in determining a minimum value of said proximal pitch for which any contact between two consecutive containers is avoided, in particular during the irradiation step during which each container is driven in rotation on itself.

Advantageously, each container is rotationally immobile during said second irradiation step.

Advantageously, said method comprises at least one preliminary setting step consisting, when the direction of displacement followed by the flow of containers is orthogonal to the main axis of the containers, in positioning said at least one emitter having a main axis according to an inclination angle which, lying between the main axis of the emitter and the axis of the container, is determined as a function of the height of the container so that the ratio of the height of the container to the height of the emitter is close to 1.

Advantageously, said at least one emitter being arranged to have an inclination angle of 90° between its main axis and the axis of a container, said method comprises at least one preliminary parameterizing step consisting in parameterizing the conveying system to vary at least the speed of displacement of the flow of containers which is transported along a path comprising a section that is inclined relative to the axis of said at least one emitter such that each container performs an upward or downward movement.

Advantageously, the irradiation step for sterilizing the containers from the outside is obtained by means of a pulsed electron beam.

BRIEF DESCRIPTION OF THE FIGURES

Other features and advantages of the invention will become apparent on reading the following detailed description, for an understanding of which reference will be made to the attached drawings, in which.

DETAILED DESCRIPTION OF THE FIGURES

Figure 1:
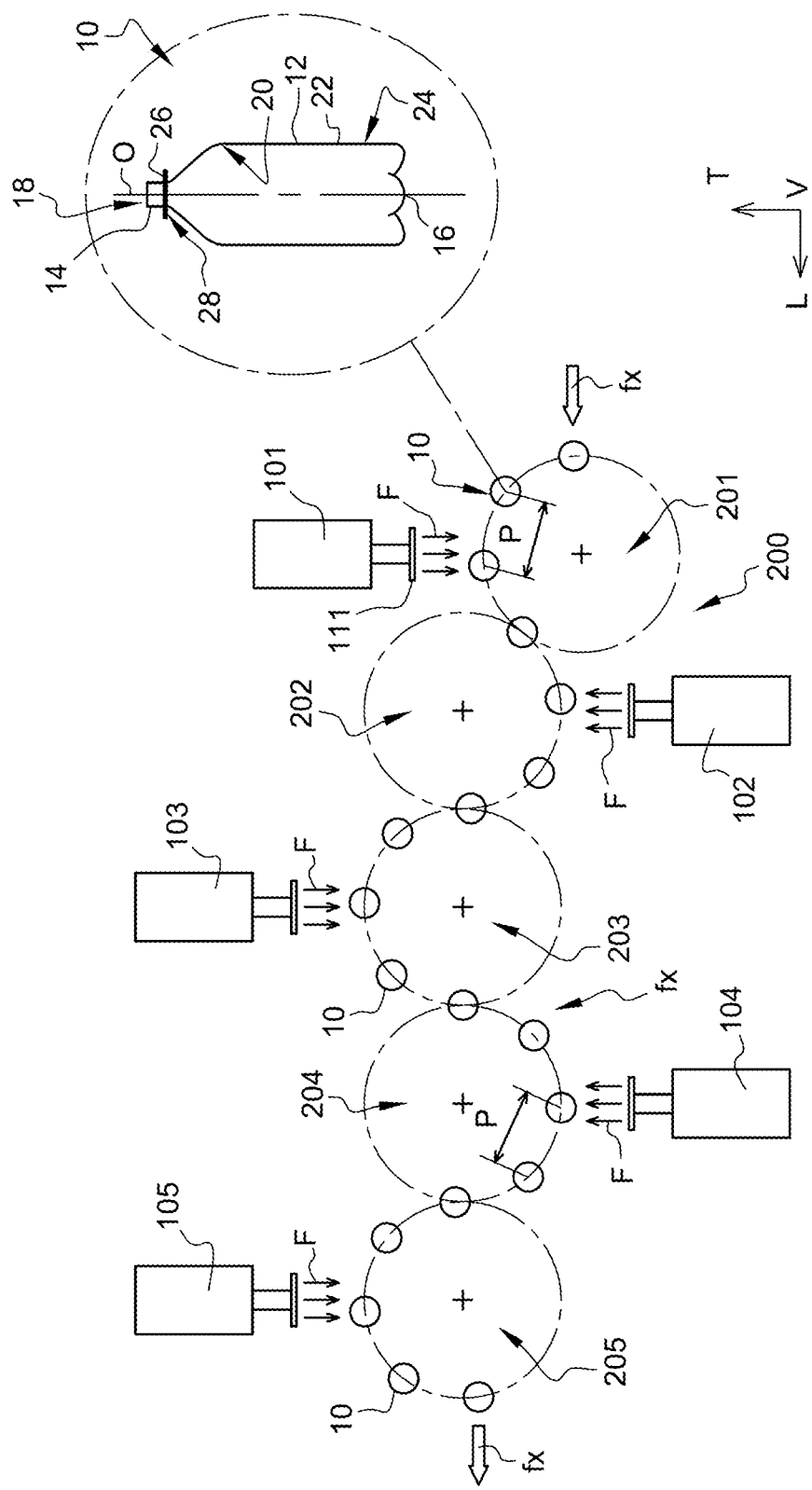
FIG. 1 is a top view which schematically represents a flow of containers made of thermoplastic material, for example bottles, which are transported with a constant pitch by a conveying system along a path along which are arranged emitters of a sterilization device that are intended to irradiate said containers from the outside with an electron beam and which illustrates the implementation of a treatment method for the sterilization by irradiation of containers according to the state of the art.

Hereinafter in the description, the longitudinal, vertical and transverse orientations will be adopted, in a nonlimiting manner, with respect to the trihedron (L, V, T) represented in the figures.

By convention, the longitudinal and transverse orientations together defining a horizontal plane are determined in a fixed manner with respect to the containers.

The terms "upstream" and "downstream" will be used in a nonlimiting manner with reference to the direction of displacement of the containers which are transported by the conveying system from upstream to downstream following a given path.

Also, the terms "upper" and "lower" or "top" and "bottom" will be used in a nonlimiting manner with reference to the vertical orientation. The terms "internal" or "external" and "inner" or "outer" are notably used with respect to the containers, the internal volume being delimited by the wall of the container whose body is provided with a neck and closed by a bottom such that said wall respectively delimits the inside and the outside.

In the following description, the elements designated by the same reference numerals designate analogous, similar or identical means.

Figure 2:
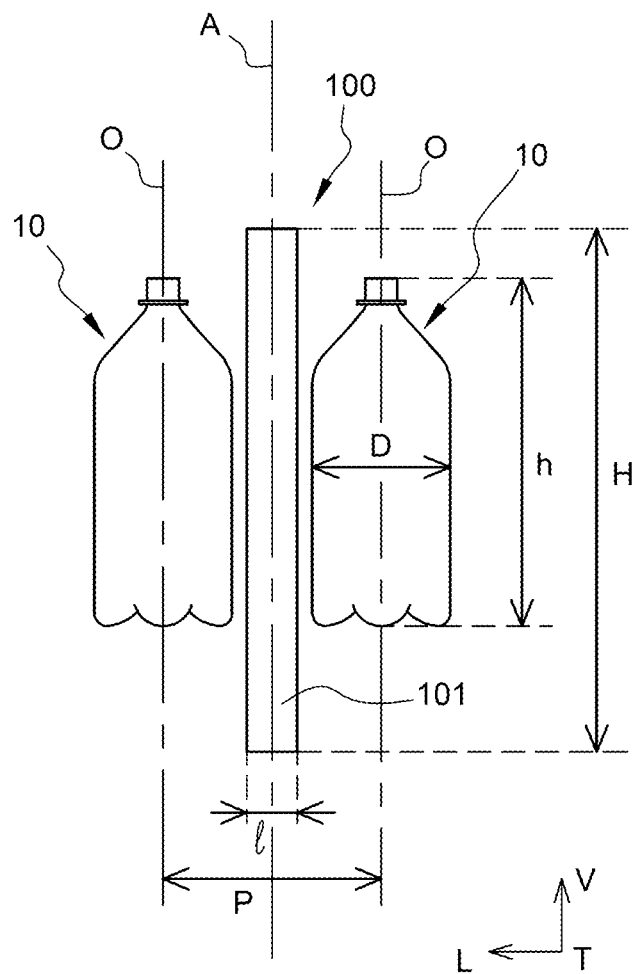
FIG. 2 is a side view which represents one of the emitters of the sterilization device according to FIG. 1 and two consecutive containers of the flow, and which illustrates a path section forming a zone of sterilization by irradiation of the containers according to the state of the art.

FIGS. 1 and 2 illustrate a sterilization device 100 for the implementation of a treatment method for the sterilization by irradiation of containers 10 according to the state of the art for the Applicant.

In the present application, the containers 10 made of thermoplastic material to be sterilized are preferentially bottles, notably made of PET (polyethylene terephthalate), manufactured from a preform. As a variant, the container 10 made of thermoplastic material is a can, a flask, a pot, etc.

As illustrated in FIG. 1, the container 10 comprises a body 12 provided with a neck 14 and closed by a bottom 16, said neck 14 circumferentially delimiting an opening 18.

The container 10 comprises an inner surface 20 delimited by a wall 22 forming the body 12, the neck 14 and the bottom 16, and an outer surface 24.

Preferably, the neck 14 of the container 10 comprises at least one collar 26 which extends radially outward and comprises a lower face 28.

The container 10 has a main axis O.

As illustrated in FIGS. 1 and 2, the axis O of the container 10 here extends vertically according to the trihedron (L, V, T).

Preferably, the containers 10 are transported in a so-called "neck up" position during their irradiation in procession by at least one electron beam (F) delivered by the sterilization device 100.

The sterilization device 100 is, for example, incorporated in an installation (not represented) for manufacturing containers in which the sterilization by irradiation of the containers 10 is thus performed.

Such an installation for manufacturing containers 10, in particular bottles made of PET, is well known from the state of the art.

The manufacture of a container made of thermoplastic material is obtained therein from a hot preform, generally previously thermally conditioned in a thermal conditioning unit or oven before being introduced into one of the molds of a molding unit (or blower) to be transformed therein by blowing by means of at least one pressurized fluid, with or without stretching.

The sterilization of the containers is therefore performed downstream of the blowing unit or blower (not represented) of such a container manufacturing installation.

In such an installation, the containers 10 (and the preforms) made of thermoplastic material are successively transported in the form of a continuous flow (fx) by a conveying system 200 through different units of the installation handling the manufacturing steps.

Such a conveying system 200 further comprises transfer wheels of which numerous embodiments are known.

As a reminder, transfer wheels comprising a notched plate associated with guiding means and transfer wheels comprising clamps controlled or not at least in opening, are primarily distinguished.

FIG. 1 thus represents a section of the path followed by the containers 10 originating from the molding unit, an arrow at each end of the section indicating the direction of circulation of the flow (fx) of containers 10, from upstream to downstream.

On the section of the path of FIG. 1, the containers 10 of the flow (fx) are transported successively by transfer wheels which, here five in number, are respectively referenced 201 to 205.

The containers 10 are transported with a determined separation, called pitch P, corresponding to the distance between the axes O of two consecutive containers 10 of the flow (fx).

On the section of the path associated with the sterilization device 100, the pitch P between two containers 10 is constant, that is to say that the pitch P does not vary between the first transfer wheel 201 situated upstream and the last transfer wheel 205 situated downstream.

According to an important feature, in addition to the pitch P between two consecutive containers 10, the speed of displacement of the containers 10 forming said flow (fx) is thus constant.

The speed of displacement of the containers 10 determines the production rate of such a manufacturing installation, expressed as a number of containers per hour, said rate being notably determined as a function of the filling unit.

The sterilization device 100 comprises emitters, here five emitters, successively referenced 101 to 105, which are each intended to irradiate said containers 10 from the outside with an electron beam F.

The emitters 101 to 105 are arranged along the path followed by the flow (fx) of containers 10, one emitter being, for example, associated with each of the transfer wheels 201 to 205.

For the implementation of a treatment method according to the state of the art, the sterilization device 100 comprises a significant number of emitters necessary to obtain an irradiation dose finally received by each container 10 which makes it possible to guarantee the sterilization thereof.

The emitters 101 to 105 are arranged on the side of the path followed by the flow (fx) of containers 10 such that the containers 10 are successively irradiated radially from the outside by each electron beam (F) emitted by one of the emitters.

Each container 10 each time receives a given irradiation dose which is notably determined by the time of exposure to said electron beam (F) and therefore by the speed of displacement of the containers 10 in front of the emitters 101 to 105.

In FIG. 1, a container 10 of the flow (fx) is successively irradiated by each of the five emitters 101 to 105 of the sterilization device 100 and finally receives a cumulative quantity of irradiation corresponding to a lethal dose for which the sterilization of the inner surface 20 and of the outer surface 24 of the container 10 is obtained.

Now, the cost of an emitter is still particularly high, which remains an obstacle for the sterilization of the containers 10 by irradiation.

This is one of the reasons why solutions are sought to optimize the use of such emitters in order, notably, to reduce the total number of emitters used, but without reducing production rates.

The emitters 101 to 105 forming said sterilization device 100 are identical such that the description of the emitter 101 provided hereinbelow is equally valid for the other emitters of the sterilization device 100.

As illustrated in FIG. 2, the emitter 101 has a main axis A which extends vertically according to the trihedron (L, V, T).

The emitter 101 has a parallelepipedal form and extends, along its main axis A, over a height H. Preferably, the emitter 101 comprises a head 111 which is more particularly represented in FIG. 2.

One emitter 101 is thus capable of irradiating, from the outside, a container 10 vertically having a height h, from its bottom 16 to its neck 14, said height h of the container 10 being less than or equal to the height H of the emitter 101.

However, while the height H of the emitter 101 is fixed, determined by construction, the size of the containers 10, for its part, varies according to the applications.

Indeed, one and the same manufacturing installation is likely to manufacture containers 10, such as bottles, ranging for example from a half-liter (or less) content to a content of two liters.

A part of the electron beam (F) emitted by the emitter 101 is therefore lost since at least a part of the container 10 is not located radially in line to be irradiated.

The lost part of the electron beam (F) emitted by an emitter is notably a function of the difference between the height H and the height h of the container 10.

That also constitutes an overhead, notably with respect to the electrical energy consumed to power the emitter producing the electron beam (F).

A treatment method for the sterilization by irradiation of containers 10 made of thermoplastic material according to the invention will be described hereinbelow, by comparison with the state of the art illustrated by FIGS. 1 and 2.

The container 10 is identical to that described previously, that is to say of the type having a main axis O and comprising a body 12 provided with a neck 14 and closed by a bottom 16.

Likewise, the treatment method according to the invention is intended to treat a flow (fx) of containers 10 transported, from upstream to downstream, by a conveying system 200 along a given path, with a determined separation, called pitch P, corresponding to the distance between the axes O of two consecutive containers 10.

According to the invention, the treatment method for the sterilization by irradiation of containers 10 made of thermoplastic material comprises at least:

- an initial step of modification of the pitch consisting in varying said initial pitch P between two consecutive containers 10 to increase the irradiation time of each container 10; and
- an irradiation step consisting in irradiating each container 10 of the flow (fx) from the outside with an electron beam (F) emitted by said at least one emitter 110 of the sterilization device 100.

Said at least one emitter 110 is arranged on a section of said path so as to form a zone of irradiation of the containers 10.

Advantageously, the irradiation step is performed after the step of modification of said initial pitch (P).

Thus, the irradiation step is performed after the step of modification of said initial pitch (P) during which the pitch (P) will be selectively varied to be able to reduce the speed of displacement of the containers 10 at least in each irradiation zone so as to increase the irradiation time of each container 10.

By comparison with the state of the art, the speed of displacement of the containers is not therefore constant along the path determined by the conveying system 200.

However, notably by virtue of the deceleration and acceleration phases implemented upon the changing of pitch, the average speed of displacement remains at least equal to that obtained in the state of the art such that the manufacturing rates are not thereby modified, in particular not reduced.

In the present invention, the step of modification of the initial pitch (P) is a temporary modification whose aim is to be able to then increase the irradiation time of each container 10.

In addition, by increasing the irradiation time, the invention also proposes optimizing the irradiation step to maximize the quantity of electrons received by a container so as to more rapidly achieve the lethal dose sought, that is to say a dose greater than or equal to 10 kGy (kilo-Gray).

Advantageously, the treatment method according to the invention comprises a final step of modification of the pitch which, contrary to the initial step of modification of the pitch, consists in once again varying the separation of the containers to reestablish said initial pitch (P) between the containers 10.

Advantageously, the speed of displacement of each container 10 is temporarily reduced at least in said irradiation zone to increase the irradiation time of each container 10 by said at least one emitter.

By virtue of the increase in the irradiation time, the irradiation dose emitted by an emitter 110 which is received by each container 10 will therefore be greater and thereby will make it possible to reduce the number of emitters needed to obtain a lethal dose.

By comparison with the state of the art described with reference to FIGS. 1 and 2, it is therefore possible to use a lesser number of emitters, for example three emitters compared to five previously, and do so without the irradiation dose received by each container 10 being in any way affected, thus preserving the degree of sterilization finally obtained.

Advantageously, the reduction of the number of emitters of the sterilization device 100 makes it possible to substantially reduce the costs of implementation of a sterilization by irradiation by means of an electron beam (F).

In fact, for a sterilization result that is at least equivalent, the reduction of the number of emitters first of all makes it possible to reduce the cost of acquisition of a sterilization device 100, notably intended to equip an installation for manufacturing containers 10.

Advantageously, the reduction of the number of emitters then makes it possible to also reduce the operating costs of a sterilization device 100, in particular the consumption of electrical energy needed to produce an electron beam (F).

Advantageously, each container 10 is driven in rotation on itself, about its axis O, at least during the irradiation step, in order for all of the container 10 to be irradiated uniformly by the electron beam (F).

Preferably, the irradiation step for sterilizing the containers 10 from the outside is obtained by means of a pulsed electron beam (F), that is to say an electron beam which is formed by a succession of pulses.

Advantageously, the pulses forming said pulsed electron beam (F) have an emission time, an intensity and an energy which are determined according to the applications.

Reference will for example be able to be made to the teachings of the abovementioned document WO-2016/120544 concerning the physical characteristics of such an electron beam (F) of pulsed type.

Figure 3:
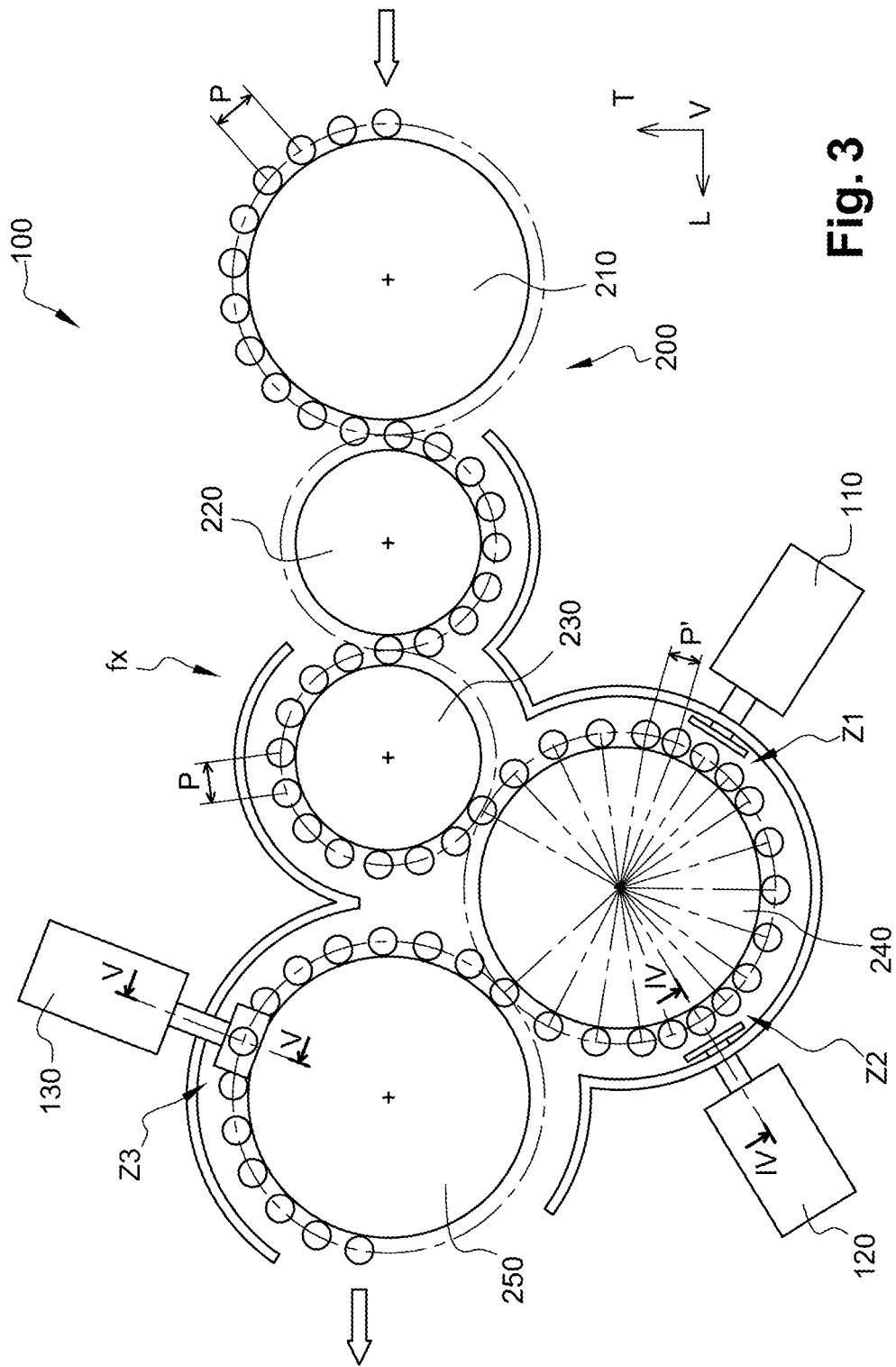
FIG. 3 is a top view which, like FIG. 1, represents a flow of containers made of thermoplastic material transported by a conveying system along a given path and which illustrates a first exemplary embodiment for the implementation of the treatment method for the sterilization by irradiation of the containers according to the invention in which the pitch between two consecutive containers is temporarily reduced in order to increase the container irradiation time.
Figure 4:
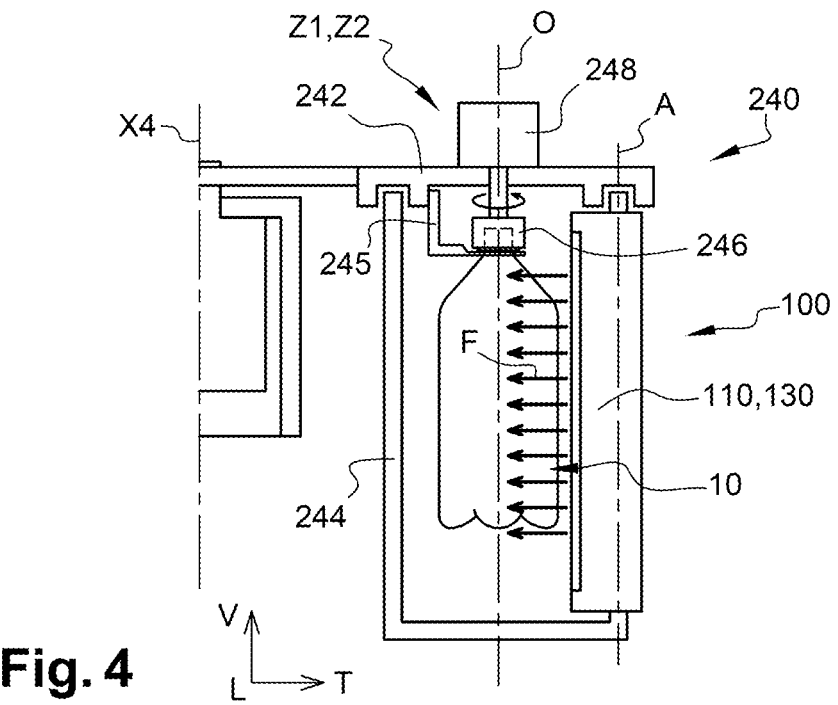
FIGS. 4 and 5 are cross-sectional views of irradiation zones of FIG. 3 which represent one of the containers during sterilization from the outside by irradiation by means of an electron beam and which illustrate, respectively, a zone of irradiation of the body of at least one container simultaneously driven in rotation on itself and another zone of irradiation of the neck of at least one container.
Figure 5:
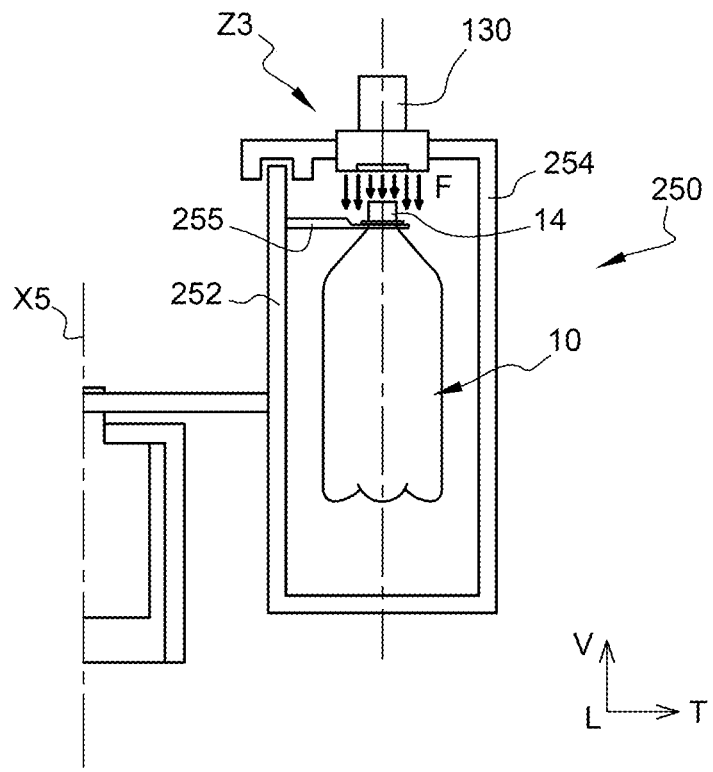

FIGS. 3 to 5 show a first exemplary embodiment for the implementation of the treatment method for the sterilization by irradiation of containers according to the invention.

In this first exemplary embodiment, the initial pitch P between two consecutive containers 10 is temporarily reduced by varying their speed of displacement, thus obtaining an increase in the irradiation time.

In this first exemplary embodiment, the initial step of modification of said initial pitch (P) consists in reducing the separation between the containers 10 of said flow (fx) by modifying the speed of the transported containers 10 in order, at least in said irradiation zone, to obtain a proximal pitch P'.

The proximal pitch P' obtained is less than the initial pitch P.

Advantageously, the initial step of modification of said initial pitch (P) comprises a phase of deceleration of the containers to obtain said proximal pitch (P').

As illustrated in FIG. 3, the containers 10 of the flow (fx) are slowed down at least upstream of each irradiation zone so that the irradiation time of each container 10 is increased, increasing the irradiation dose received by the containers.

Preferably, the treatment method comprises a preliminary determination step consisting, as a function of the maximum outside diameter D of a container 10, in determining a minimum value of said proximal pitch (P').

Advantageously, said minimum value is not zero, said proximal pitch (P') being determined so as to avoid any contact between two consecutive containers 10.

Each container 10 is thus able to be driven in rotation on itself, about its axis O, during the irradiation step, and without interference with the adjacent containers 10 respectively situated upstream and downstream.

The treatment method comprises a final step of modification of the pitch consisting, after said at least one irradiation step, in once again varying the separation of the containers 10 to reestablish said initial pitch (P) between the containers 10 of said flow (fx).

To do this, the final step of modification of the pitch comprises at least one acceleration phase.

Preferably, said irradiation step is performed dynamically on the flow (fx) of containers 10 which are transported along said path in such a way that their speed varies but without ever reaching a zero value.

Advantageously, the speed of displacement of the containers 10 varies jointly with the modification of said pitch, decreasing during the deceleration phase then increasing next during the acceleration phase, but without the container 10 ever being stopped.

FIGS. 3 to 5, illustrating a first example sterilization device 100 for the implementation of the treatment method according to the invention, will now be more particularly described.

FIG. 3 represents a section of the path followed by the flow (fx) of containers 10, notably in a container manufacturing installation, said section being then situated upstream of the filling unit and preferably downstream of the blowing unit.

Advantageously, the irradiation step is performed on empty containers 10 leaving the blowing unit which, after their sterilization by irradiation by means of electrons, are then filled in the filling unit.

The flow (fx) of containers 10 is conveyed by a conveying system 200 successively comprising transfer wheels, respectively referenced 210 to 250.

The first transfer wheel 210 is fed with containers 10, according to the arrow represented in FIG. 3, originating for example from the blowing unit or from a labeling unit (not represented) situated upstream.

The containers 10 are transported with an initial pitch P at least by the first transfer wheel 210, the second transfer wheel 220 and the third transfer wheel 230.

As illustrated in FIG. 3, the initial pitch P corresponds to the separation between two successive containers 10, to the distance between the respective axes O of said containers 10.

Preferably, the sterilization device 100 comprises at least one first emitter 110 and one second emitter 120 which are arranged to irradiate the containers 10 from the outside, more particularly to irradiate at least the body 12 and the bottom 16 of each container 10.

The first emitter 110 and the second emitter 120 are, here, associated with the fourth transfer wheel 240 of the flow (fx) of containers 10.

The first emitter 110 and the second emitter 120 are arranged radially, here outside, the fourth transfer wheel 240, on the side of the path followed by the containers 10.

The first emitter 110 and the second emitter 120 are each arranged on a section of the path of the containers 10 so as to form a first irradiation zone Z1 and a second irradiation zone Z2.

The first emitter 110 and the second emitter 120 are intended for the implementation of a first irradiation step that said irradiation step of the treatment method comprises.

Advantageously, said irradiation step comprises a first irradiation step consisting in irradiating, from the outside, at least the body 12 of each container 10 with the electron beam (F) emitted by said at least one emitter, here successively by the first emitter 110 and the second emitter 120.

The first emitter 110 and the second emitter 120, respectively having a main axis (A), are arranged relative to said path of the containers 10 in such a way that said main axis (A) of each emitter is substantially coaxial with the main axis (O) of the container during the irradiation.

Advantageously, each container 10 is driven in rotation on itself about its axis O during said first irradiation step so as to circumferentially irradiate all of the container 10.

Advantageously, the sterilization device 100 also comprises a third emitter 130 which, here, is associated with the fifth transfer wheel 250.

The third emitter 130 is arranged on a section of the path of the containers 10 so as to form a third irradiation zone Z3.

The third emitter 130 is arranged to irradiate the containers 10 from the outside, more particularly to irradiate at least the neck 14 of each container 10.

Preferably, the third emitter 130 is arranged plumb with, here above, the path followed by the flow (fx) of containers 10 transported by the fifth transfer wheel 250 of the conveying system 200.

Advantageously, said irradiation step of the method comprises a second irradiation step consisting in irradiating at least the neck 14 of each container 10 with an electron beam (F) emitted by at least one other emitter, here said third emitter 130.

The third emitter 130, having a main axis (A), is arranged relative to said path in such a way that said main axis (A) of the emitter is substantially orthogonal to the main axis (O) of the irradiated container 10.

Each container 10 is advantageously immobile in rotation during said second irradiation step.

FIG. 4 shows a cross-sectional view produced at the second emitter 120 on a plane IV-IV illustrated in FIG. 3, said plane extending vertically and radially by passing through the axis (X4) of rotation of the fourth transfer wheel 240.

The first emitter 110 and the second emitter 120 are identical such that the description of FIG. 4 given hereinbelow with reference to the second emitter 120 is also valid for the first emitter 110.

Preferably, the fourth transfer wheel 240 comprises protection means which, associated at least with the first emitter 110 and the second emitter 120, surround the containers 10 to form a containment enclosure.

Advantageously, the protection means comprise movable protection means 242 which are driven in rotation about the axis (X4) of rotation and fixed protection means 244 which are immobile relative to the flow (fx) of containers 10.

Preferably, the part of the first emitter 110 and the part of the second emitter 120 respectively emitting an electron beam (F) are incorporated in said fixed protection means 244.

In the fourth transfer wheel 240, the containers 10 are transported via gripping means 245 which, linked to radial arms, are driven about the axis X5 of rotation.

Preferably, the gripping means 245 comprise clamps intended to each cooperate with a part of the neck 14 of the container 10 and which can be controlled selectively in opening.

The fourth transfer wheel 240 comprises means 246 for driving each container 10 in rotation on itself, about its main axis O.

The rotational driving means 246 comprise a driving element configured to cooperate with a part of the neck 14 of each container 10, for example a mandrel which is housed in the opening 18 of the neck 14.

The driving means 246 can be driven in rotation by actuation means 248, such as a motor.

Preferably, the gripping means 245 are controlled in opening so as not to radially clamp the neck 14 of the container 10 in order to allow them to be freely driven in rotation by the driving means 246.

As illustrated in FIG. 3, the speed of each container 10 of the flow (fx) is slowed down at least upstream of the first irradiation zone Z1 so as to modify the pitch thereof, to reduce the separation between two consecutive containers 10.

Advantageously, the irradiation time of each container 10 is thus increased since the exposure time of the container 10 to the electron beam (F) emitted by the emitter is increased.

The deceleration phase then makes it possible to switch from the initial pitch P to a proximal pitch P' which is less than said initial pitch P. That is why the containers 10 are grouped together, brought close to one another, in front of the first emitter 110 and then in front of the second emitter 120.

The initial step of modification of the pitch makes it possible to increase the irradiation time of the containers 10 when the containers 10 pass through the first irradiation zone Z1 with a speed less than their average speed of displacement.

Advantageously, the slowdown following the deceleration phase is then offset by at least one equivalent acceleration phase, in accordance with a final step of modification of the pitch, so as to reestablish said initial pitch P.

The variation of pitch between the containers 10 is, for example, produced using control means of mechanical type, notably with cam and roller.

In a variant, the means for controlling the variation of pitch are electrical, for example a motor, preferentially a linear motor.

The same variation of pitch, from initial pitch (P) to the proximal pitch (P'), is produced in the second irradiation zone Z2, the containers 10 successively undergoing a deceleration phase to increase the irradiation time by the electron beam (F) and then an acceleration phase.

Preferably, the deceleration phase is primarily performed outside of said first irradiation zone Z1 and second irradiation zone Z2, but can continue therein.

Similarly, the acceleration phase is primarily performed outside of said first irradiation zone Z1 and second irradiation zone Z2 but can begin therein.

The irradiation of the containers 10 is also increased by modification of the separation of the containers 10 which are juxtaposed alongside one another when the separation is equal to the proximal pitch P'.

In fact, and by comparison with FIG. 2 illustrating the state of the art, the electron beam (F) then does not encounter any empty space between two consecutive containers 10 so that the use of the electrons produced by an emitter is optimized.

The conveying system 200 is configured to vary the pitch of the containers 10 on said fourth transfer wheel 240 so that the average speed of displacement of the containers 10 remains unchanged.

Advantageously, the flow (fx) of containers 10 present, at the output of the fourth transfer wheel 240, a separation between two consecutive containers 10 corresponding to the initial pitch (P).

Preferably, irradiation of the neck 14 of the container 10 on the one hand and of the body 12 on the other hand are performed successively and not simultaneously.

The irradiation of the necks 14 is performed on the fifth transfer wheel 250 via the third emitter 130 of the sterilization device 100.

Like the fourth wheel 240, the fifth transfer wheel 250 preferentially comprises protection means, respectively movable protection means 252, which are driven in rotation about the axis (X5) of rotation and fixed protection means 254 which are immobile relative to the flow (fx) of transported containers 10.

Preferably, the part of the third emitter 130 emitting the electron beam (F) is incorporated in an upper part of said fixed protection means 254.

On the fourth transfer wheel 240, the driving of the container 10 in rotation being performed by the neck 14, the driving means 246 are then likely to mask a part thereof from the electron beam (F) such that there is a risk that the neck 14, although irradiated, is not perfectly sterilized.

That is why a specific irradiation of the neck 14 of each container 10 is implemented.

Advantageously, the irradiation of the neck 14 is performed after that of the body 12. Thus, even in case of contamination of the neck 14, for example by the rotational driving means 246, the subsequent irradiation of the neck 14 makes it possible to guarantee a perfect sterilization of the container 10.

During the irradiation of the neck 14, the container 10 is held in "neck up" position via gripping means 255 which are configured to leave the neck 14 disengaged, freely irradiated by the electron beam (F) emitted by the third emitter 130.

By comparison with the step of irradiation of the container 10 performed on the fourth transfer wheel 240 by the first emitter 110 and the second emitter 120, the container 10 is not driven in rotation on itself during the irradiation of the neck 14 performed by the third emitter 130 on the fifth wheel.

Preferably, the step of irradiation of the necks 14 is performed on a transfer wheel other than that of the bodies 12 and on containers 10 having said initial pitch P.

Obviously, the description which has just been given of the successive irradiation of the body 12 then the neck 14 of each container 10 should not be interpreted in a limiting manner but as targeting more particularly a part of the container 10 since the electron beam (F) emitted by each of the emitters 110, 120 and 130 irradiates all of the container 10.

In the first example illustrated in FIGS. 3 to 5, the emitters 110 and 120 are arranged in such a way that the main axis A of the emitter extends vertically, coaxially to the axis O of each of the containers 10.

Now, as explained in the preamble with reference to FIG. 2, an emitter has a height H that is determined by construction while the height h of the manufactured containers 10, for its part, varies according to the applications.

Thus, when the container 10 has a height h which is half the height H of the emitter, half of the electron beam (F) emitted by the emitter is then lost since this part of the beam (F) does not irradiate any container.

To remedy this, the invention proposes two variant arrangements of an emitter making it possible to further enhance the sterilization obtained by increasing, for an equivalent irradiation time, the irradiation dose received by each container 10.

By comparison to the state of the art, such an increase in the dose of electrons received by the container 10 advantageously contributes to reducing the number of emitters by making optimal use of the emitted electron beam (F).

Figure 6:
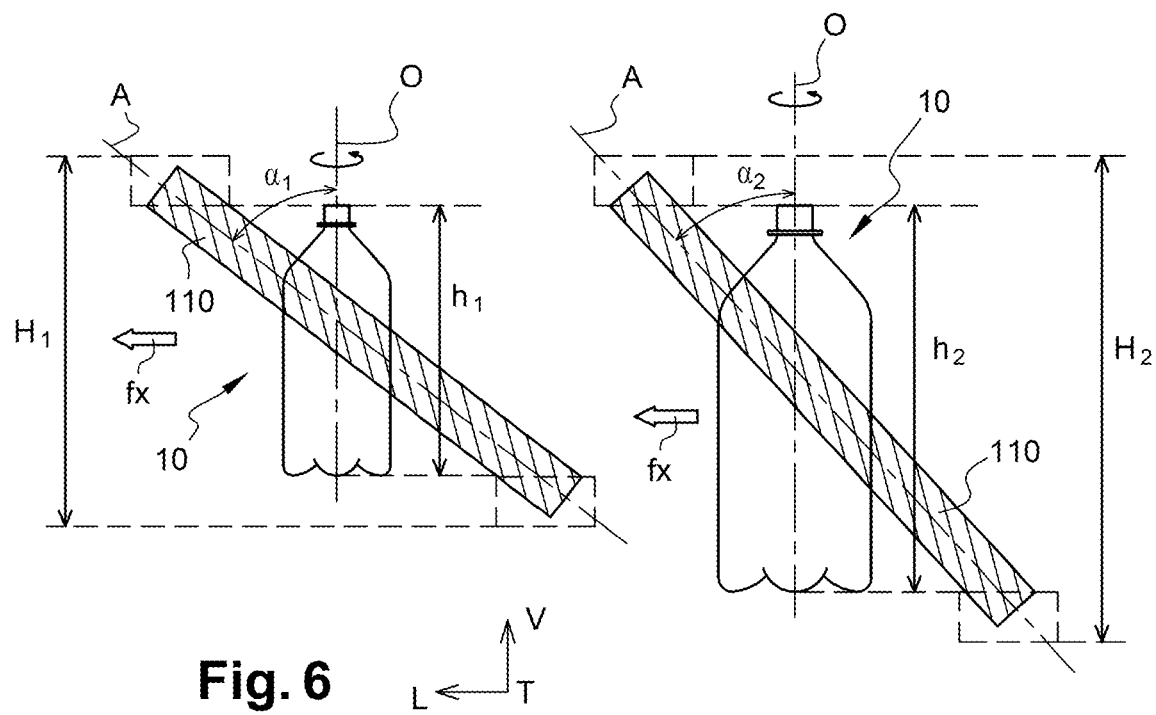
FIG. 6 is a side view which, similar to FIG. 2, represents a first variant embodiment consisting in optimizing the arrangement of the emitters relative to the containers as a function of their dimensions, in particular their height, and which illustrates, for two containers of different dimensions, an inclination of the emitter with respect to the axis of the container by an angle that is determined to optimize the irradiation of said container.

FIG. 6 represents a first variant embodiment consisting in optimizing the arrangement of said at least one emitter, such as the first emitter 110 and the second emitter 120, relative to the container 10 as a function if its dimensions, in particular its height h.

FIG. 6 shows two containers 10 of different dimensions, a first container 10 having a height h1 and a second container 10 having a height h2, greater than the height h1 of the first container.

To optimize the irradiation of a container 10 and limit the losses of electrons emitted by an emitter, the emitter is inclined relative to the container as a function of the height of the container 10 such that the ratio of the height H of the container to the height h of the emitter is close to 1.

An angle of inclination is thus determined that corresponds to the angle (α) formed by the intersection of the main axis A of the emitter and the axis O of the container, the direction of displacement followed by the container which is illustrated by an arrow in FIG. 6 being orthogonal to the main axis O of the container.

Advantageously, the emitter is configured to incline by the angle (α) a head that said emitter comprises, said head forming the terminal part emitting said electron beam (F) irradiating at least one container 10.

As illustrated in FIG. 6, the emitter 110 is for example inclined by an angle (α1) of inclination lying between its main axis A and the axis O of the container 10 of height (H1) or inclined by an angle (α2) of inclination lying between its main axis A and the axis O of the container 10 of height (H2).

The angle (α) of inclination of the emitter thus varies as a function of the container 10 to be irradiated, the value of said angle (α) being determined to optimize the irradiation of said container by the electron beam (F), to maximize the irradiation dose received.

Preferably, the emitter 110 is inclined such that the two ends extend respectively beyond the neck 14 and the bottom 16 of the container 10, said ends of the emitter 110 having been represented in FIG. 6 by dotted line rectangles.

Advantageously, the neck 14 and the bottom 16 of the container 10 are thus irradiated optimally by the electron beam (F) emitted by the part of the emitter 110 located radially opposite.

Advantageously, the container 10 is driven in rotation on itself, about its axis O, during its irradiation by the electron beam (F) emitted by the emitter 110.

Advantageously, the treatment method according to the invention comprises at least one preliminary setting step consisting in positioning said at least one emitter having a main axis A according to an angle (α) of inclination which, lying between the main axis A of the emitter and the axis O of the container, is determined as a function of the height (H) of the container transported in a direction of displacement which is orthogonal to the main axis O of the container.

Figure 7:
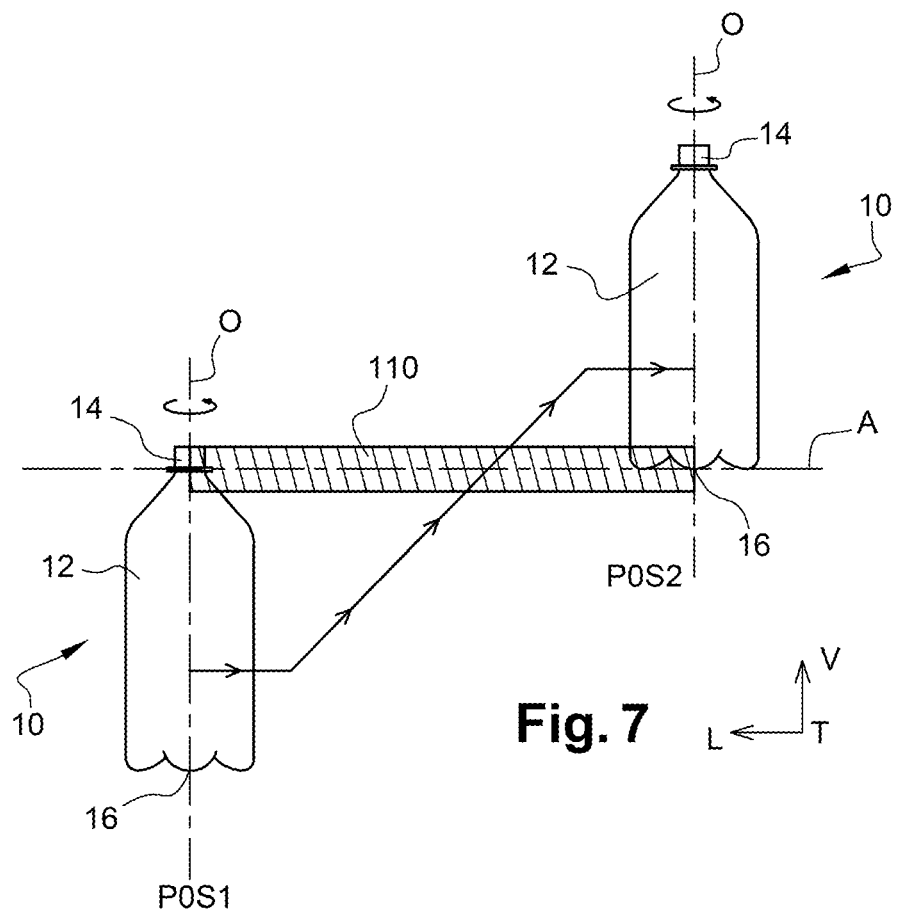
FIG. 7 is a side view which represents a second variant embodiment consisting in optimizing the irradiation of the containers relative to the emitters and which illustrates an emitter arranged horizontally whose axis is orthogonal with respect to the axis of the container, said container being driven in rotation on itself and transported to pass in front of the emitter by performing an oblique displacement, by an upward or downward movement, at a speed which varies as a function of the type of container.

FIG. 7 represents a second variant embodiment for optimizing the irradiation dose by adjusting the relative arrangement between an emitter, such as the first emitter 110, and the flow (fx) of containers 10.

As illustrated in FIG. 7, the emitter 110 is arranged horizontally according to the trihedron (L, V, T) such that the main axis A of the emitter is orthogonal with respect to the axis O of the container 10, each container 10 being, as previously, transported in so-called "neck up" position.

Advantageously, the container 10 is driven in rotation on itself, about its axis O, during its irradiation by the electron beam (F) emitted by the emitter 110.

The rotation driving means, like the means for gripping the container 10, have not been represented in FIG. 7, but are, for example, similar to those described with reference to FIGS. 3 to 5.

FIG. 7 represents, on the left, a container 10 in a first, so-called low position POS1, in which the neck 14 of said container 10 is facing the emitter 110.

FIG. 7 represents, on the right, this container 10 in a second, so-called high position POS2, in which the bottom 16 of said container 10 is located facing the emitter 110 to be irradiated by the electron beam (F) emitted by said emitter 110.

Advantageously, the first, so-called low position POS1, makes it possible to more particularly irradiate the neck 14 while the second, so-called high position POS2, makes it possible to more particularly irradiate the bottom 16.

In fact, the neck 14 and/or the bottom 16 are very sensitive parts, sometimes difficult to sterilize, for example because of the thickness of the thermoplastic material or the petaloid form for a bottom 16.

Between the first, so-called low position POS1, and the second, so-called high position POS2, the container 10 is transported to pass in front of the emitter 110 by performing a displacement comprising at least one portion of trajectory that is oblique in the irradiation zone.

Depending on the direction of the displacement, the container 10 performs either an upward movement from the first, so-called low position POS1, to the second, so-called high position POS2, or, conversely, a downward movement from the second, so-called high position POS2 to the first, so-called low position POS1.

Preferably, the speed of each container 10 is not constant over said oblique portion of trajectory lying between said first, so-called low position POS1 and second, so-called high position POS2.

Advantageously, the speed of the container 10 therefore varies in the irradiation zone lying between said first, so-called low position POS1 and second, so-called high position POS2.

The speed of the container 10 can in particular be reduced to selectively increase the irradiation time of a part of the container 10.

As an example, the speed of the container 10 is minimal when the container 10 is in said first, so-called low position POS1 and/or second, so-called high position POS2, in order to increase the irradiation time of the neck 14 and/or of the bottom 16 of the container 10.

Preferably, the step of irradiation of the containers 10 is performed dynamically on a container 10 that is still moving, whether the speed varies or is constant.

Obviously, the speed of the container 10 could also be temporarily nil, each container observing, for example, a stop in said first, so-called low position POS1 and/or second, so-called high position POS2.

FIG. 7 represents only two containers 10 to illustrate said first, so-called low position POS1 and second, so-called high position POS2, but, and according to the invention, an initial step of modification of the pitch is advantageously performed before the irradiation step.

According to the first example described with reference to FIGS. 3 to 5, the containers 10 of the flow (fx) have, for example in the irradiation zone, a proximal pitch (P') which is less than the initial pitch (P).

Advantageously, the treatment method according to the invention comprises at least one preliminary parameterizing step consisting, with said at least one emitter having a main axis A being arranged horizontally with an angle (α) of inclination of 90° between the main axis A of the emitter and the axis O of the container, in parameterizing at least the speed of displacement of the flow (fx) of containers in the irradiation zone.

Advantageously, in addition to the speed of displacement, the speed with which each container 10 is driven in rotation on itself is also a parameter which is determined according to the applications.

The path of the containers 10 in the irradiation zone is followed in a direction which, not being orthogonal to the main axis O of the containers, corresponds to an upward or downward movement to optimize the irradiation of the containers.

By comparison with the variant of FIG. 6, in this variant, the emitter 110 occupies a fixed horizontal position which remains the same regardless of the dimensions of the container 10, notably the height h of the container.

In this variant according to FIG. 7, the optimization of the irradiation of the container 10 is obtained by a parameterizing of the speed of displacement of the container in the irradiation zone.

For each container 10, it is thus possible to optimize the irradiation step to selectively vary the irradiation time as a function of the type of container 10, to increase, for example, the dose received by the neck 14 and/or the bottom 16 of the container 10 or even a specific part of the body 12.

Figure 9:
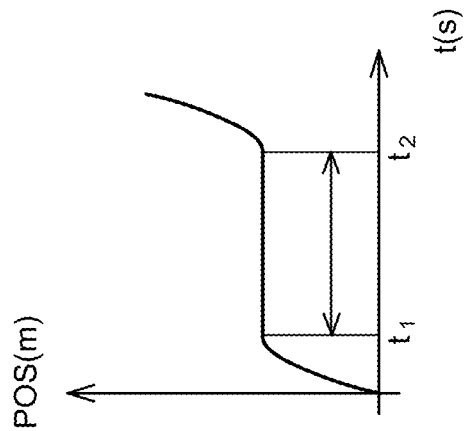
FIG. 9 is a curve which represents, for the second exemplary embodiment according to FIG. 8, the variation of the position POS (m) of a container as a function of time t (s) and which illustrates the variation of the speed of each container occurring, after the division of the flow of containers, in the first and second irradiation zones.
Figure 8:
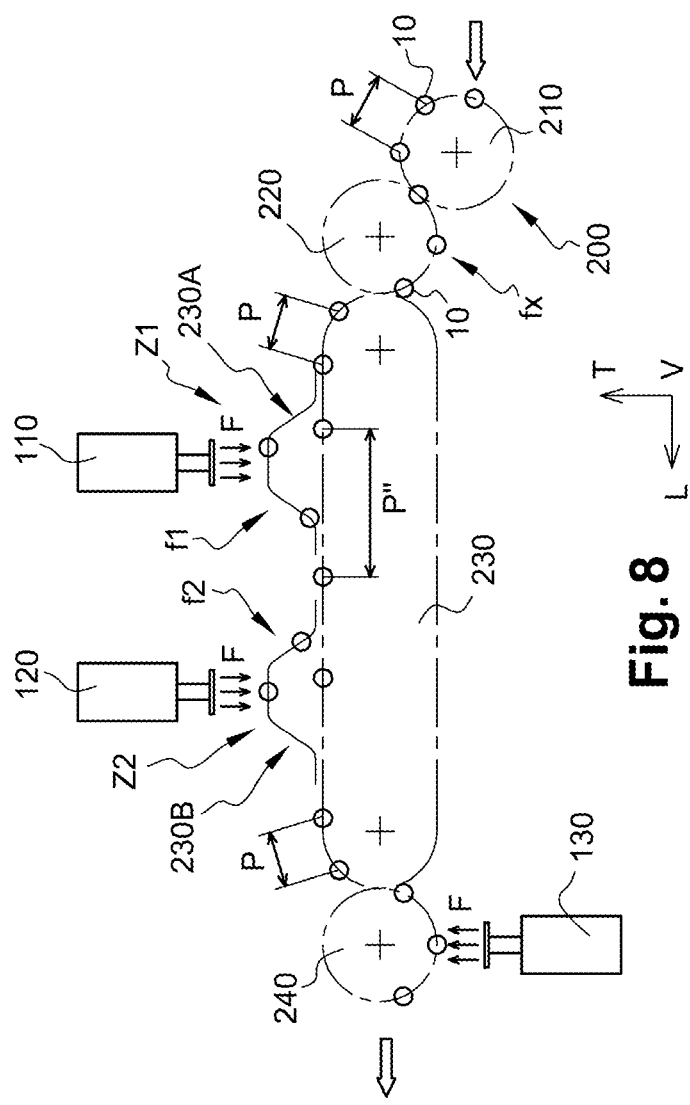
FIG. 8 is a top view which, like FIGS. 1 and 3, represents a flow of containers made of thermoplastic material transported by a conveying system following a given path and which illustrates a second exemplary embodiment for the implementation of the treatment method for the sterilization by irradiation of the containers according to the invention, in which a division of the flow of containers is effected before then varying the pitch between two consecutive containers to increase the irradiation time thereof.

FIGS. 8 and 9 show a second exemplary embodiment for the implementation of the treatment method for the sterilization by irradiation of containers according to the invention.

In this second exemplary embodiment and according to the invention, the step of irradiation of the containers 10 is implemented after the initial step of modification of the pitch.

According to this second example, the treatment method comprises a step of division of the flow (fx), implemented prior to the step of modification of said initial pitch (P), consisting in dividing the flow (fx) of transported containers 10.

FIG. 8 shows, as previously for FIG. 1 or 3, a sterilization device 100.

By virtue of the invention and as in the first example, the number of emitters of the sterilization device 100 is advantageously reduced to three emitters compared to five emitters in the state of the art according to FIGS. 1 and 2.

The sterilization device 100 thus comprises a first emitter 110 and second emitter 120, respectively intended to irradiate at least the body 12 of the containers 10, and a third emitter 130 intended to irradiate at least the neck 14 of the containers.

By comparison, the flow (fx) of containers 10 is transported by a conveying system 200 comprising a first transfer wheel 210, a second transfer wheel 220 and a fourth transfer wheel 240.

In this second example, the third "wheel" of the conveying system 200 is modified and produced in the form of a transfer device 230 having an elongate track form.

The transfer device 230 comprises an overall rectilinear path section, fed upstream by the second wheel 220 and feeding the fourth wheel 240 downstream.

The transfer device 230 comprises, on said rectilinear section, a first bypass section 230A and a second bypass section 230B, with which the first emitter 110 and the second emitter 120 are respectively associated.

As illustrated in FIG. 8, the first emitter 110 arranged to the side of the first bypass section 230A forms a first irradiation zone Z1 while the second emitter 120 arranged to the side of the second bypass section 230B forms a second irradiation zone Z2.

The structure and the operation of the third emitter 130 associated with the fourth transfer wheel 240 and more particularly intended to irradiate the neck 14 of the containers 10 is similar to the description given for the first example, to which reference will advantageously be made.

The containers 10 circulate from upstream to downstream according to the arrows represented in FIG. 8, the transported containers 10 of the flow (fx) having, on the first transfer wheel 210, the second transfer wheel 220 and the fourth transfer wheel 240, a separation corresponding to the initial pitch (P).

The step of division of the flow (fx) of containers 10 is performed on the transfer device 230.

Advantageously, the flow (fx) of containers 10 is divided into at least:
- a first flow (f1) of containers which are transported to the first irradiation zone Z1 comprising at least the first emitter 110, and
- a second flow (f2) of containers which are transported to the second irradiation zone (Z2) comprising at least one second emitter 120.

Preferably, the flow (fx) of containers is divided at a rate of one container 10 in two to respectively form said first flow (f1) and said second flow (f2).

After the division step, the separation between two consecutive containers 10 of one or other of said first and second flows (f1, f2) is then equal to a distal pitch (P") which corresponds to twice the initial pitch (P).

By comparison with the first example, at the end of the division step, the containers 10 are not closer to one another but, on the contrary, further apart.

By virtue of this increase in the separation or pitch between two consecutive containers 10 of each of said first and second flows (f1, f2), it is then possible to more greatly vary the speed of each container 10, and do so without risk of interference with the containers 10 situated immediately upstream and downstream.

After the division of the flow (fx) of containers, the initial step of modification of the pitch is advantageously implemented.

The initial step of modification of the pitch comprises at least one deceleration phase to reduce the speed of each of the containers 10 forming one of said at least first flow (f1) and second flow (f2) at least in said associated first irradiation zone Z1 and second irradiation zone Z2.

Each container 10 thus passes in front of one of the emitters 110 or 120 with a reduced speed, even advantageously zero speed, so as to increase the irradiation time of each container 10 and consequently the dose of electrons received.

Preferably, the container 10 is temporarily stopped in front of the emitter of the first irradiation zone Z1 like that of the second irradiation zone Z2, that is to say that its speed is momentarily zero.

By virtue of the significant reduction of the speed, even the temporary stopping of the container 10, it is possible to irradiate at least the body 12 of each container 10 by making use of a single emitter, the first emitter 110 and the second emitter 120 being here disposed parallel.

By comparison, in the first example, the body 12 of each container 10 is irradiated twice, successively by the first emitter 110 then by the second emitter 120, said second emitter 120 being disposed in series with the first emitter 110.

The step of modification of the pitch also comprises at least one acceleration phase to increase the speed of each of the containers 10 of said first and second flows (f1, f2) in order to retain the same average conveying speed of the containers 10.

Advantageously and as previously, the manufacturing rates in the case of an installation are not therefore impacted by the speed variations implemented in order to increase the irradiation time of each container 10.

Advantageously, an acceleration phase is performed respectively upstream and downstream of the emitter in each of said first and second irradiation zones Z1, Z2 to be able to further maximize the irradiation time.

FIG. 9 shows a curve to illustrate the variation of the speed undergone by a container 10 circulating in one of the bypass sections 230A, 230B of the transfer device 230.

The curve of FIG. 9 represents the distance traveled POS (m) by a container 10 as a function of time t(s).

As illustrated by the first part of said curve, the container 10 first of all undergoes a first acceleration phase for a time t1.

On the median part of the curve, a deceleration phase can be seen which ends with the stopping of the container 10 in front of the emitter, so between the points t1 and t2 the container 10 does not in fact travel any additional distance.

When the irradiation time of the container 10 corresponding to (t2-t1) has ended, the container 10 then once again undergoes an acceleration phase.

The irradiated container 10 continues its path over that of the bypass sections 230A, 230B on which it was located until it rejoins the main section of the transfer device 230 where the first flow (f1) and the second flow (f2) combine to reform the flow (fx) of containers 10.

Advantageously, the method comprises a final step of modification of the pitch consisting in combining the first flow (f1) and the second flow (f2) to reform a flow (fx) of containers 10 once again having said initial pitch (P).

For a sterilization device 100 according to FIG. 8, the conveying system 200 is advantageously a system using shuttles with which linear motors are associated.

As a nonlimiting example, a conveying system of the "acopos trak" type developed by the company B&R/industrial automation, can be used to ensure the dividing of the flow and the speed variations for the irradiation, individually, for each transported container.

Obviously, one or other of the variant embodiments described previously with reference to FIGS. 6 and 7 for maximizing the irradiation dose received by a container 10 over a given time, can advantageously be incorporated in a sterilization device 100 according to FIG. 8 for the implementation of the second exemplary embodiment of the treatment method according to the invention.

The invention lends itself to industrial application and proposes a treatment method for the sterilization by irradiation of containers 10 made of thermoplastic material, comprising at least:
- an initial step of modification of the pitch consisting in selectively varying the initial pitch P between two consecutive containers 10 to increase the irradiation time of each container 10;
- an irradiation step consisting in irradiating each container 10 from the outside with an electron beam F emitted by at least one emitter 110, 120, 130 of a sterilization device 100.

The invention claimed is:
1. A treatment method for the sterilization by irradiation of containers (10) made of thermoplastic material of the type having a main axis (O) and comprising a body (12) provided with a neck (14) and closed by a bottom (16), wherein the containers (10) forming a flow (fx) are transported by a conveying system (200) along a given path, with a determined separation, called initial pitch (P), corresponding to the distance between the axes (O) of two consecutive containers (10), and wherein an initial speed of displacement of the containers (10) forming said flow (fx) is constant, the treatment method comprising at least:
  modifying the pitch consisting in varying said initial pitch (P) between two consecutive containers (10) to increase the irradiation time of each container (10);
  irradiating each container (10) of the flow (fx) from the outside with an electron beam (F) emitted by at least one emitter (110, 120, 130) of a sterilization device

(100) which is arranged on a section of said path so as to form a zone (Z1, Z2, Z3) of irradiation of the containers (10).

2. The treatment method as claimed in claim 1, wherein the modifying of said initial pitch (P) consists in reducing the separation between the containers (10) of said flow (fx) by reducing the speed of the transported containers (10) to obtain, at least in said irradiation zone, a proximal pitch (P') which is less than the initial pitch (P).

3. The treatment method as claimed in claim 2, wherein the modifying of said initial pitch (P) comprises at least one phase of deceleration of the containers to obtain said proximal pitch (P').

4. The treatment method as claimed in claim 2, wherein the method further comprises
modifying the pitch comprising at least one acceleration phase to once again vary the separation of the containers (10) in order to reestablish said initial pitch (P) between the containers (10) of said flow.

5. The treatment method as claimed in claim 1, wherein said method further comprises dividing the flow (fx), implemented prior to the modifying of the pitch, consisting in dividing the flow (fx) of transported containers (10), into at least:
a first flow (f1) of containers which are transported to a first irradiation zone (Z1) comprising at least one first emitter (110) capable of emitting an electron beam (F) and
a second flow (f2) of containers which are transported to a second irradiation zone (Z2) comprising at least one second emitter (120) capable of emitting an electron beam (F).

6. The treatment method as claimed in claim 5, wherein the flow (fx) of containers is divided at a rate of one container (10) in two to form, respectively, said first flow (f1) and said second flow (f2) such that the separation between two consecutive containers (10) of one or other of said first flow (f1) and second flow (f2) is then equal to a distal pitch (P") which is greater than the initial pitch (P).

7. The treatment method as claimed in claim 5, wherein, after the division of the flow (fx) of containers, the modifying of the initial pitch (P) comprises decelerating, during a deceleration phase, to reduce the speed of each of the containers (10) forming one of said at least first flow (f1) and second flow (f2) at least in said associated first irradiation zone (Z1) and second irradiation zone (Z2).

8. The treatment method as claimed in claim 7, wherein, after the dividing of the flow (fx) of containers, said step of modification of the initial pitch (P) comprises at least one acceleration phase to selectively increase the speed of each of the containers (10) of said first flow (f1) and second flow (f2), respectively upstream and/or downstream of said first irradiation zone (Z1) and second irradiation zone (Z2).

9. The treatment method as claimed in claim 6, wherein said method further comprises:
modifying the pitch consisting, after said irradiating, in merging the containers (10) of said first flow (f1) and second flow (f2) to obtain a flow (fx) of containers (10) having said initial pitch (P) between two consecutive containers (10).

10. The treatment method as claimed in claim 1, wherein said irradiating comprises a first irradiation step consisting in irradiating from the outside at least the body of each container (10) with the electron beam (F) emitted by said at least one emitter (110, 120) having a main axis (A).

11. The treatment method as claimed in claim 10, wherein, when a direction of displacement followed by the flow (fx) of containers (10) is orthogonal to the main axis (O) of the containers (10), said at least one emitter (110, 120) is arranged relative to said path in such a way that said main axis (A) of the emitter is substantially coaxial with the main axis (O) of the irradiated container (10).

12. The treatment method as claimed in claim 10, wherein, when a direction of displacement followed by the flow (fx) of containers (10) is orthogonal to the main axis (O) of the containers (10), said at least one emitter (110, 120) is inclined by an inclination angle (a) which, lying between the main axis (A) of the emitter and the axis (O) of the container, is determined as a function of the height (H) of the container so that the ratio of the height (H) of the container to the height (h) of the emitter is equal to about 1.

13. The treatment method as claimed in claim 10, wherein, when a direction of displacement followed by the flow (fx) of containers (10) comprises at least one section that is inclined relative to the axis (A) of said at least one emitter (110, 120) such that each container (10) performs an oblique displacement by an upward or downward movement, said at least one emitter (110, 120) is arranged horizontally to have an inclination angle (a) of 90° between its main axis (A) and the axis (O) of a container.

14. The treatment method as claimed in claim 10, wherein each container (10) is driven in rotation on itself about its axis (O) during at least said first irradiation.

15. The treatment method as claimed in claim 10, wherein said irradiating further comprises at least one second irradiating of at least the neck (14) of each container (10) with an electron beam (F) emitted by said at least one emitter (130) which, having a main axis (A), is arranged plumb with the containers (10) along said path.

16. The treatment method as claimed in claim 3, wherein the method further comprises
modifying the pitch comprising at least one acceleration phase to once again vary the separation of the containers (10) in order to reestablish said initial pitch (P) between the containers (10) of said flow.

17. The treatment method as claimed in claim 6, wherein, after the division of the flow (fx) of containers, the modifying of the initial pitch (P) comprises decelerating, during a deceleration phase, to reduce the speed of each of the containers (10) forming one of said at least first flow (f1) and second flow (f2) at least in said associated first irradiation zone (Z1) and second irradiation zone (Z2).

18. The treatment method as claimed in claim 5, wherein said method further comprises:
modifying the pitch consisting, after said irradiating, in merging the containers (10) of said first flow (f1) and second flow (f2) to obtain a flow (fx) of containers (10) having said initial pitch (P) between two consecutive containers (10).

19. The treatment method as claimed in claim 2, wherein said irradiating comprises a first irradiation step consisting in irradiating from the outside at least the body of each container (10) with the electron beam (F) emitted by said at least one emitter (110, 120) having a main axis (A).

20. The treatment method as claimed in claim 15, wherein each container (10) is driven in rotation on itself about its axis (O) during at least said first irradiation step.

* * * * *